United States Patent [19]
Charvin et al.

[11] Patent Number: 5,662,714
[45] Date of Patent: Sep. 2, 1997

[54] DEVICE FOR EXTENDING LIVING TISSUES

[75] Inventors: Guy Charvin, Antibes; Patrick Frechet, 92, Avenue Mozart, 75016 Paris, both of France

[73] Assignees: M.X.M., Antibes; Patrick Frechet, Paris, both of France

[21] Appl. No.: 603,195

[22] Filed: Feb. 20, 1996

Related U.S. Application Data

[63] Continuation of Ser. No. 184,964, Jan. 21, 1994, abandoned.

[51] Int. Cl.$^6$ ........................................... A61F 2/10
[52] U.S. Cl. .............................. 623/15; 606/213; 606/215; 606/187
[58] Field of Search ........................ 623/7–8, 15, 66; 606/213, 215–221, 187

[56] References Cited

U.S. PATENT DOCUMENTS

| | | | |
|---|---|---|---|
| 679,993 | 8/1901 | Ross | 606/123 |
| 2,012,755 | 7/1935 | De Muth | 606/217 |
| 2,421,193 | 8/1947 | Gardner | 606/215 |
| 2,472,009 | 8/1949 | Gardner | 606/216 |
| 2,575,205 | 11/1951 | Brown | 606/204.35 |
| 2,619,084 | 11/1952 | Brown | 606/204.35 |
| 2,669,747 | 2/1954 | Detaranto | 606/216 |
| 4,007,743 | 2/1977 | Blake | 623/11 |
| 4,535,772 | 8/1985 | Sheehan | 606/217 |
| 4,676,245 | 6/1987 | Fukuda . | |
| 4,955,395 | 9/1990 | Manders . | |
| 4,976,726 | 12/1990 | Haverstock | 606/213 |
| 4,994,073 | 2/1991 | Green | 606/213 |
| 5,263,971 | 11/1993 | Hirshowitz et al. | 606/216 |
| 5,441,540 | 8/1995 | Kim | 623/66 |
| 5,507,775 | 4/1996 | Ger et al. | 606/216 |

FOREIGN PATENT DOCUMENTS

| | | |
|---|---|---|
| 0279534 | 8/1988 | European Pat. Off. . |
| 0432743 | 6/1991 | European Pat. Off. . |
| 0418970 | 12/1910 | France ........................... 606/216 |
| 3738859 | 5/1985 | Germany . |
| 1412751 | 7/1988 | U.S.S.R. ........................ 606/216 |
| 9321849 | 11/1993 | WIPO . |

OTHER PUBLICATIONS

Scalp Extension from Patrick Frechet, Dermatol Surg Oncol Magazine (1993).
"Hair Transplantation" (pp. 504 to 518).
"Scalp Flexibility", Dr. Richard C. Shiell, 1992.
Advertising for "Koken".
"Focus", Facial Plastic Surgery Today, Third Quarter, 1990.

Primary Examiner—John G. Weiss
Assistant Examiner—Bruce E. Snow
Attorney, Agent, or Firm—Dvorak & Orum

[57] ABSTRACT

The technical field of the invention is that of making surgical materials implantable in the human body. The extender device (2) comprises at least two independent resilient members (8) each having at least one end fixed to at least one of two fastening members (7), enabling the device (2) to be fixed in a living tissue along the edges (13) of an area of the tissue that is to be treated. The edges are opposite each other in the direction in which they are moved towards each other at least by the resilient members and the device further includes a common support (9) to which the opposite ends of said resilient ends (8) are connected. The members (8) deform and move relative to the common support (9) so as to entrain the fastening members (7) over the support, urging them towards each other.

10 Claims, 5 Drawing Sheets

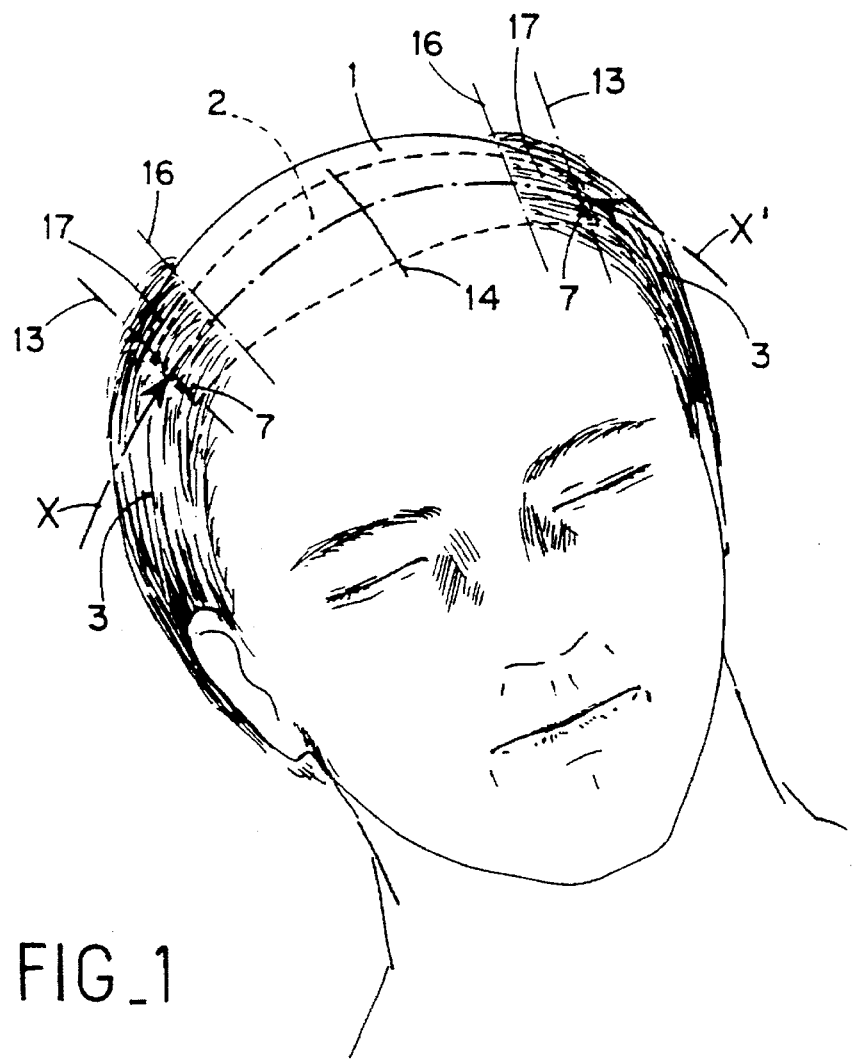
FIG_1
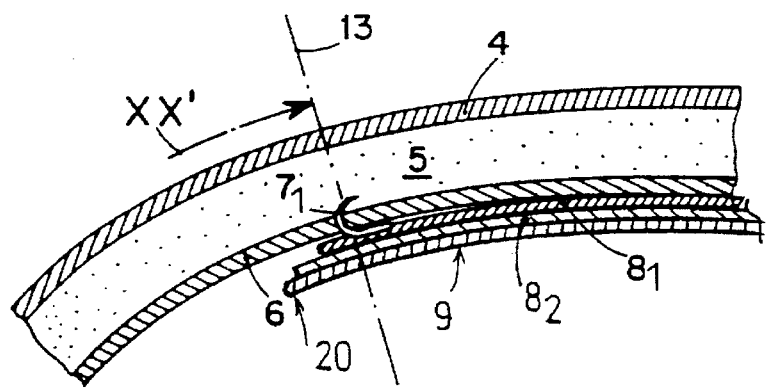
FIG_2

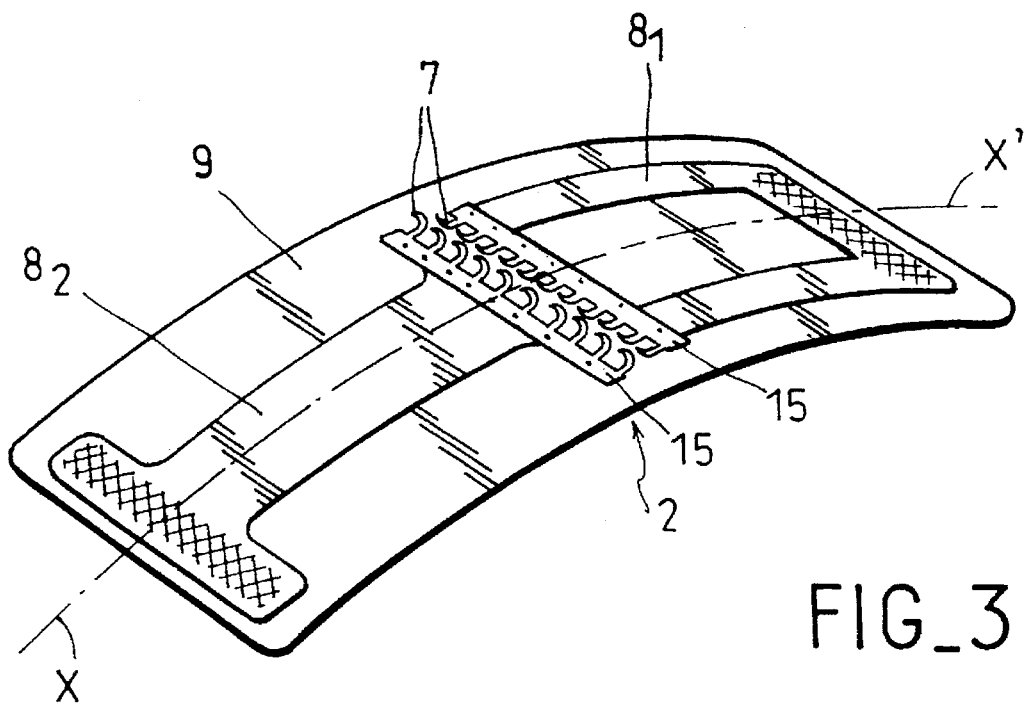
FIG_3
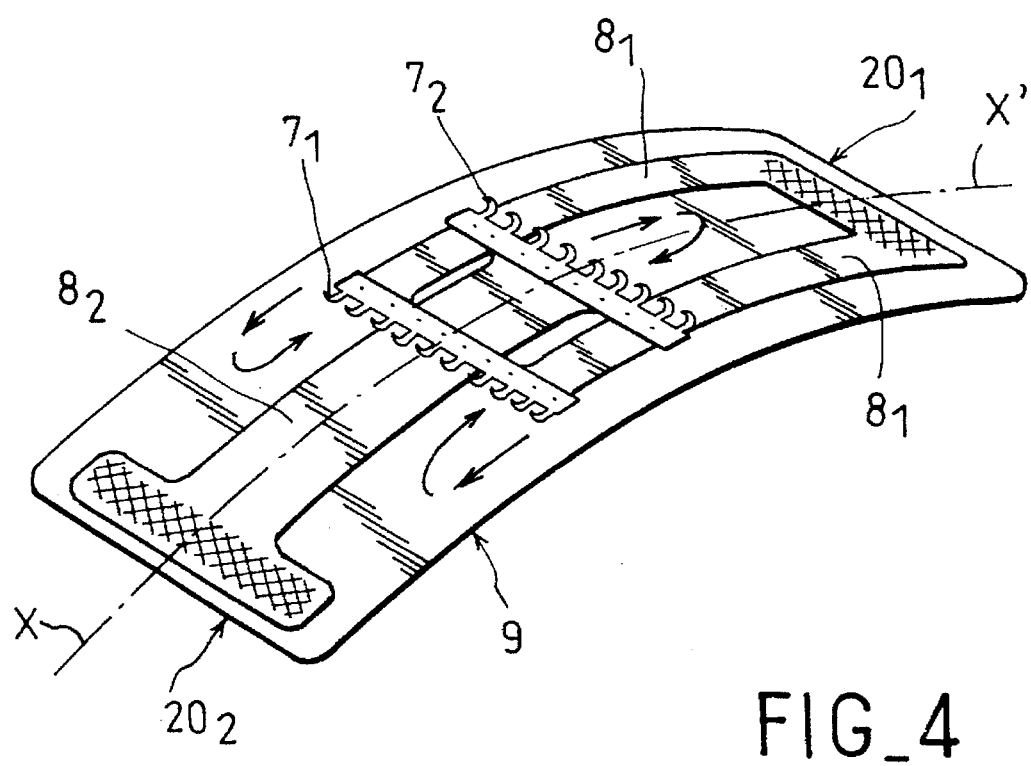
FIG_4

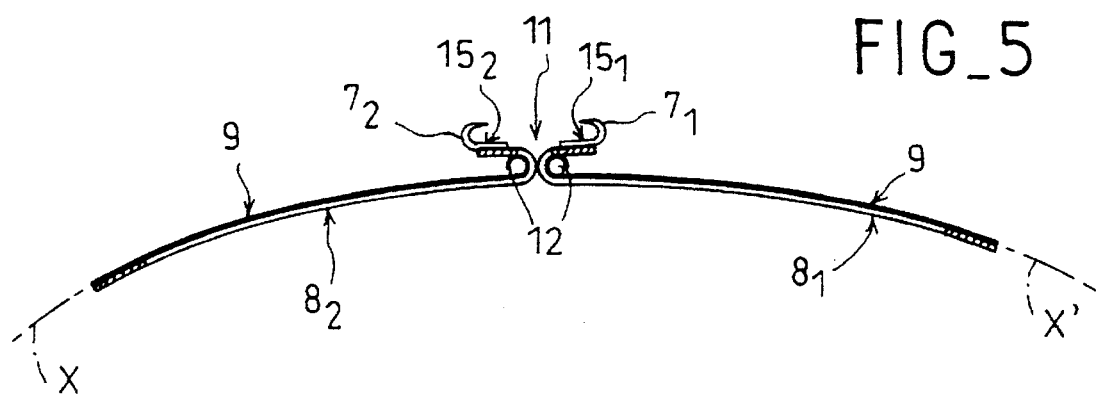
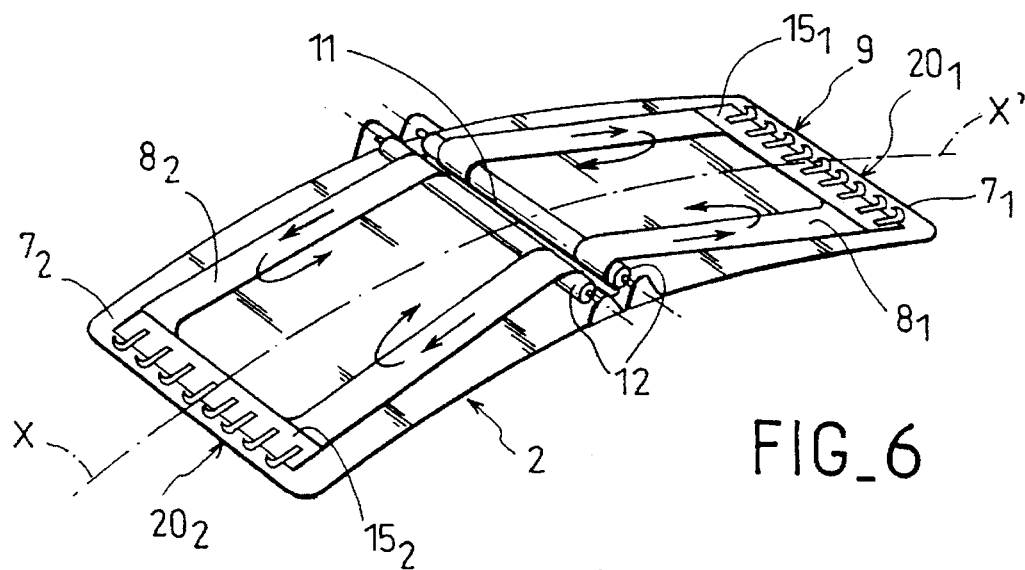
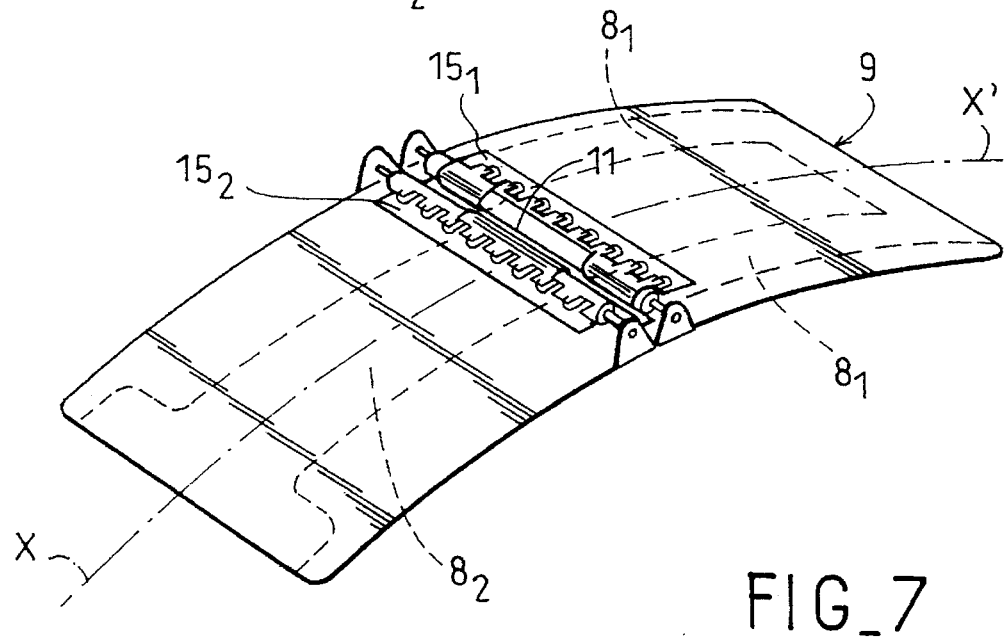

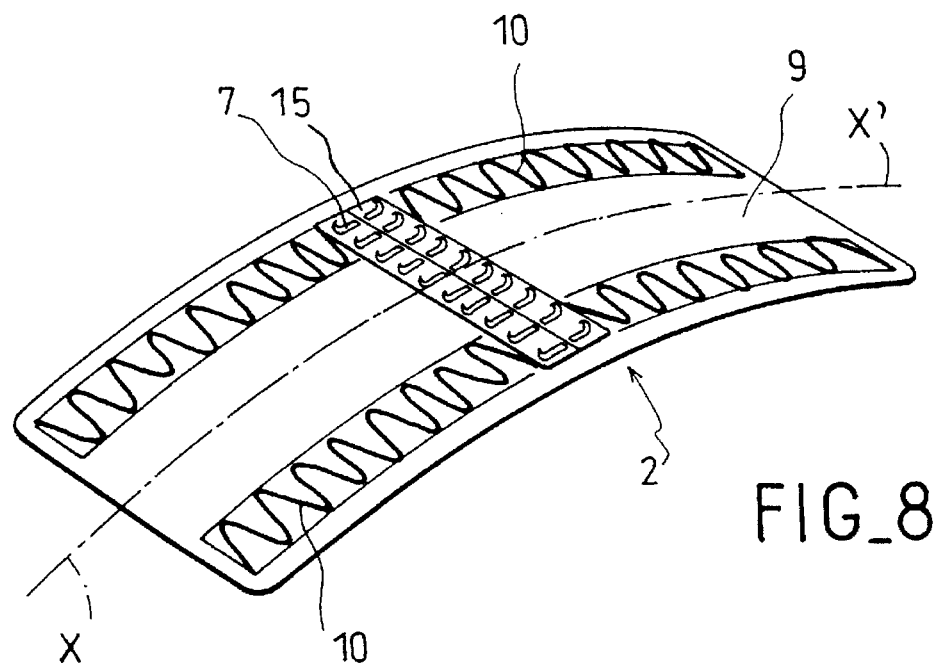
FIG_8
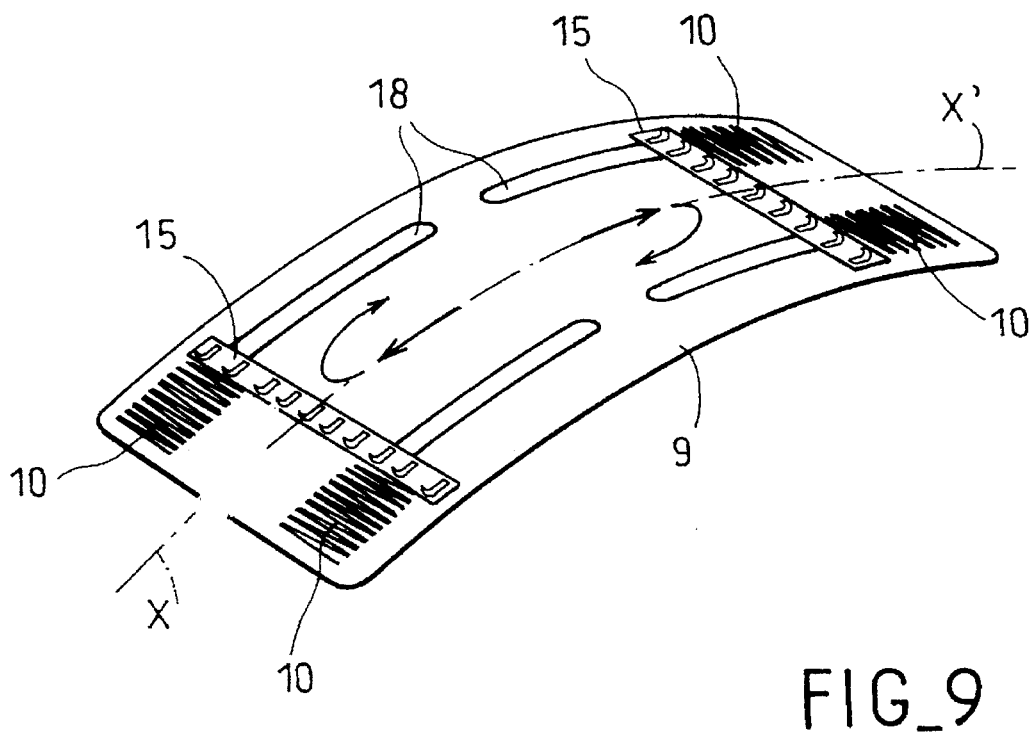
FIG_9

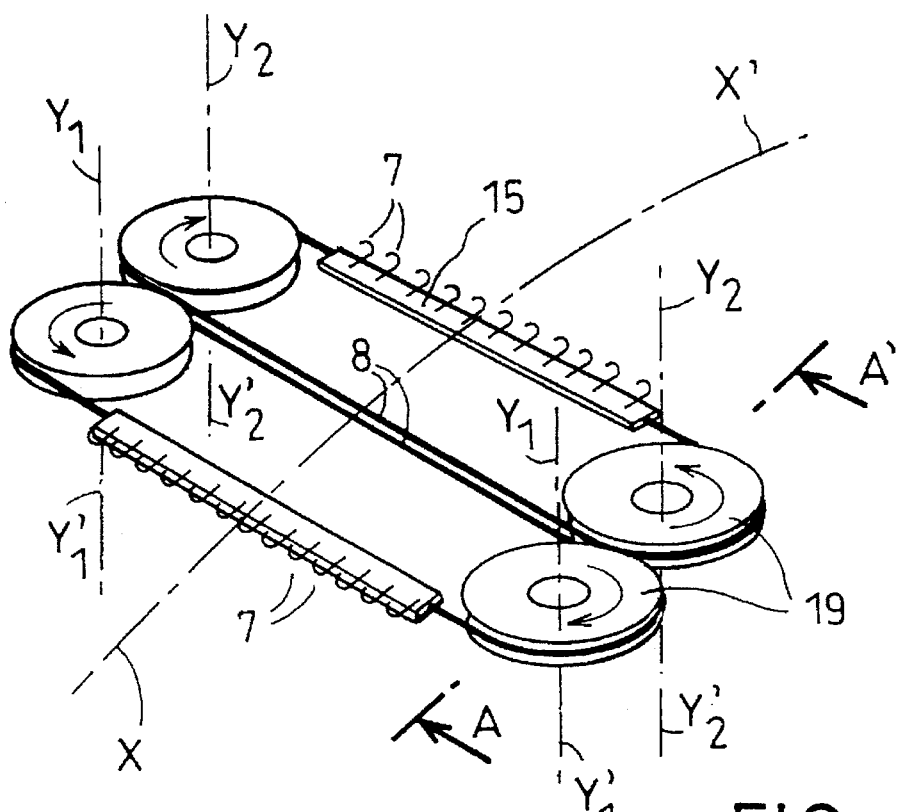
FIG_10
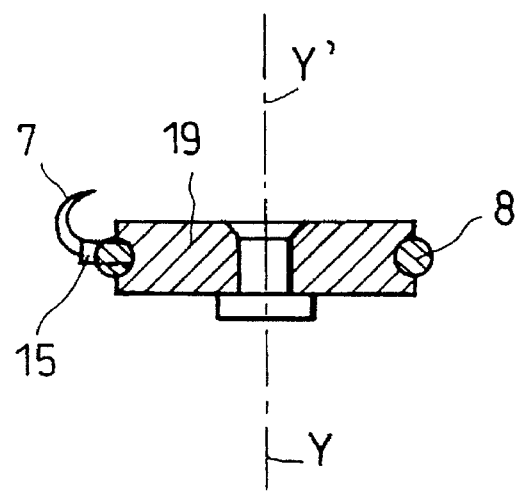
FIG_11

DEVICE FOR EXTENDING LIVING TISSUES

This application is a continuation of application Ser. No. 08/184,964, filed Jan. 21, 1994, abandoned.

The present invention relates to improvement to devices for extending living tissue, such as those described in patent application WO 93/21849 published on Nov. 11, 1993, and to which various references are made herein.

FIELD OF THE INVENTION

The technical field of the invention is that of making materials that are surgically implantable in the human body.

BACKGROUND OF THE INVENTION

One of the main applications of the invention, as in the above earlier application, is making extender devices that are implantable for a determined length of time beneath the scalp to diminish baldness, but other applications can be envisaged for the device of the invention wherever it is useful and/or necessary to stretch tissue, e.g. for diminishing wounds where it is necessary to be able to cover a damaged area with new skin, in particular when the original skin has been destroyed or damaged by burning, trauma, etc. . . .

With respect to so-called "male-pattern baldness", it is known that definitive hair loss affects one in three of men aged 50.

Such baldness forms a part of a group of conditions known medically as "cicatricial alopecias": it is related to progressive and premature atrophy of hair follicles, at the roots of individual hairs, and its origins are genetic and hereditary.

So far, no medical treatment has managed to treat male-pattern baldness, and no therapeutic solution of a medical kind can be considered earlier than age 30 to 50.

At present the only effective therapy is surgical, and more than 2 million Americans have had recourse to such surgery: this is done by surgically redistributing a fraction of healthy follicles that are genetically programmed to last throughout life. In practice, they constitute hair taken from around the tonsure.

For this purpose, essentially there are three techniques, namely: implants; reductions of the tonsure; and flaps; all three of which consist in moving healthy hair-carrying scalp to replace all or part of the bald scalp.

The present invention relates solely to the second and most recent technique of reducing tonsure; it makes it possible to achieve a clear improvement in results for extensive male-pattern baldness which constitute the major fraction of cases to be treated.

At present, three surgical techniques are used with or without special devices, each having success relating to the result obtained and satisfaction and appreciation of the people concerned:

The oldest method consists in directly eliminating a region of bald skin during a plurality of successive operations, in separating the margins of the wound from underlying portions of the scalp, and in moving the two edges of the wound towards each other from opposite sides of said wound. The two edges of the wound are closed together under tension by means of surgical sutures, thereby stretching the scalp and thus increasing the hair-carrying area at the expense of bald area. Thus, on average, it is possible to eliminate a 3 cm wide strip of bald scalp on each operation: four to six tonsure-reducing operations are then often required since there is a limit to skin elasticity and it is not reasonable to remove more than 3 cm at a time without running the risk of tearing. Nevertheless, in spite of this high number of operations, and even if said number is increased, the result cannot be improved any further, and it is possible in this way to eliminate only about half of the initially bald area.

That failure to reduce the bald scalp area completely is related to two important phenomena that are combined, that are well known, and that are already analyzed in the patent application referred to in the introduction. That surgical method of reducing tonsure therefore always leaves a region of baldness, and it is therefore necessary for it to be associated with implants, thereby naturally increasing the cost and the overall time of the procedure.

To eliminate the above phenomena, a second operative method was developed about 10 years ago, particularly in America, in which use is made of balloons placed beneath the hair-carrying scalp, which balloons are progressively inflated at regular intervals of time: the hair-carrying scalp is thus subjected to internal pressure and it expands and spreads. Once it is deemed to have been expanded sufficiently, the operation can be performed as described above by removing a strip of the bald region or even all of it, and the lips of the remaining zones can be sewn together edge-to-edge, in the proper place.

It is thus possible to eliminate the entire bald area, replacing it with the hair-carrying zones that have been expanded by the balloons. Nevertheless, it is necessary to expand the balloons themselves regularly two or three times a week in order to achieve progressive expansion of the hair-carrying skin without tearing it. This requires regular monitoring, and in any event the resulting deformation of the head makes that technique unusable on a large scale. The advantage of the technique is lost because of considerations and criteria relating to appearance and because of the difficulty in immobilizing people who must be isolated over long periods. In addition, there is always the danger of the balloon bursting and of the expansion regions being poorly monitored.

In order to avoid the above drawbacks, a third surgical method has been developed that makes use of special extender devices constituting the subject matter of the patent application mentioned in the introduction, which method has been developed over some time and has been tested with success. Such an extender device includes at least one resilient means whose external dimensions when in the active, extended position, are such that a fraction of its perimeter corresponds substantially to and overlies the edges of at least a fraction of the area of tissue to be treated. The resilient means is associated with at least two fastening means each secured to a respective opposite end of the device in the resilient direction of said resilient means, enabling the device to be fixed to said tissue along said edges.

Because such extender devices (also called "extenders" for short) provide selective surface stretching, good tonsure-reducing results are obtained with few operations, while retaining satisfactory appearance of the head during the treatment so as to enable the persons concerned to continue all normal activity. This is achieved without destroying follicles by ischemia of the surface layers of the hair-carrying scalp, as has been observed when using other techniques. When using such extenders, the same advantages of stretching living tissue such as hair-carrying scalp are to be found as when using balloons, but in this case, the enormous advantage lies in the fact that the progressive distortion and stretching of the scalp is obtained without any increase in volume, and thus without increasing area in unwanted directions, with the increase in area being obtained solely in given directions. There is thus no change to the apparent shape of the head when the tissue being stretched is hair-carrying scalp, and there is no stretching in directions that are not useful.

Furthermore since the active ends of the extender can be located exactly at the edges of the regions that are to be subjected to traction in order to change surface area, those regions that are not to be stretched are not subjected directly to said tension: thus, when stretching the scalp, there is no secondary stretching of bald areas, thereby improving the effectiveness of the system and the rapidity of its action. However, it is necessary to apply traction to hair-carrying regions that are distant from the edge of the bald region so that when extension is complete, i.e. when the extender has returned to its rest position, its ends then being at a certain distance apart, said distance corresponds to the length of hair-carrying regions situated and maintained within the ends.

Since such extender devices do not make it possible to move the ends close enough together or even into contact, it is necessary:

either, as mentioned above, to apply traction to the hair-carrying scalp from regions of tissue situated behind the actual edges of the bald regions so as to leave some of the hair-carrying scalp between the fastening systems, thereby giving rise to non-uniform stretching between treated regions situated beyond said fastening systems and non-stretched regions situated between them;

or else to perform at least one second operation and to finish off final uniting of the hair-carrying regions by an operation of the oldest type, as described above, but that may give rise to a scar that remains quite visible.

In the examples described in the document mentioned in the introduction, the lengthening capacity of the resilient means that interconnect that at least two fastening means requires a minimum rest width of said resilient means, thus corresponding to a distance of a size that may be proportional to the amount of extension capacity desired. This distance can indeed be reduced by fixing the fastening systems to wide supports that extend behind the fastening systems relative to their lines of fixture to the scalp and thus to their lines of traction, and by fixing the ends of the resilient means interconnecting the supports to the supports behind their fixing lines: it is thus possible to have resilient means of a length such that, firstly when at rest the two fixing lines of the fastening systems are as close to each other as possible, being at a fixed distance apart or even one against the other, and secondly, in extension, the longation obtained corresponds to that looked-for so that the two fastening systems are put into place at the edge of the region to be treated, which may then correspond to the region of hair-carrying scalp, while leaving only the bald region between the fastening means.

Nevertheless such a device of the earlier invention has two independent hook-supporting plates and the force urging them towards each other as applied to them by the resilient means which interconnects them tends to cause them to tilt relative to each other and thus relative to the surface of the tissue and of the scalp, and this can give rise to additional unattractive appearance; furthermore they are not very easy to put into place and since the supports are relatively large in area they give rise to frictional resistance to displacement, thereby slowing down the return of the fastening means to their rest position, thus increasing the duration of treatment.

OBJECTS AND SUMMARY OF THE INVENTION

The problem posed is thus firstly, as in the above-mentioned earlier invention, to make it possible to increase a given area of living tissue by a determined amount by lengthening it, taking advantage of the ability of cells to reproduce, while limiting secondary stretching of regions that it is not desired to stretch, with this being done using a minimum number of operations over as short a possible a period time, and secondly to make it possible to move the edges of the surfaces of tissue concerned towards each other to any desired distance apart, or even to make them touch each other, one at least of said surfaces having been lengthened, this being done using the simplest possible implementation and with uniform effective lengthening of the entire area of the tissue concerned, and as in the preceding case, without unattractive deformation of the volume of the portion of the body that is covered by said tissue.

A solution to the problem posed is an improvement to known devices for extending living tissue, comprising at least one resilient means and at least two fastening means enabling said device to be fixed in said tissue along the edges of the area thereof that is to be treated, which edges are opposite each other in the direction in which they are to be moved towards each other at least by said resilient means; according to the invention, the device for expanding living tissue further comprises at least two independent resilient means, each fixed at at least one end to at least one of the fastening means, together with at least one support that is quasi-rigid and that is stationary compared with said tissue, to which support at least one of said resilient means is secured, which means deforms and moves relative to said support over which it urges said fastening means towards each other. Said support of biocompatible material is preferably common to the resilient means and is constituted by a deformable plate of small thickness, which may itself be made up of two or more plates assembled together over adjustable lengths and deformed to match the surface of said tissue to be treated, and on which there are secured the other ends of said resilient means that are not themselves secured to the fastening means.

In an embodiment, said resilient means are constituted by parallel resilient strips that are spaced apart from one another such that the strips constituting one of said resilient means pass freely between the strips constituting the other of said resilient means, the ends of one set of strips being fixed firstly towards a first end edge of the plate and secondly to one of the fastening means such that extension of the resilient means enables the said fastening means to be displaced towards the opposite second end edge of the support, and the ends of the other resilient means are similarly fixed firstly to said second end edge and secondly to the other fastening means, the resilient means associated therewith enabling said other fastening means to be displaced towards the first edge of the support.

In another embodiment, in which the support is a plate, said support plate includes at least one through slot extending parallel to the directions of the fastening means for fastening along the edges of the tissue to be treated, each of which resilient means extends from the same edge of the support as the associated fastening means, but over the opposite face of the support, through the slot, and back over the same face of the support to where it is fixed to the fastening means.

The result is novel extender devices for extending living tissue, using the same principles as the extender devices described in the earlier application mentioned in the introduction, but having novel and specific characteristics that improve those earlier devices. The characteristics of the present invention make it possible to solve the problem posed and to eliminate the drawbacks that could be observed in the prior devices: in particular, it is thus possible to move the edges of the tissue concerned (e.g. hair-carrying scalp) together by any amount and even as closely as possible, merely by moving the edges of the bald region towards each other while stretching the entire hair-carrying regions uniformly but without leaving any portion thereof between the fastening systems, thus eliminating the need for a secondary operation. By using the devices of the present invention, a single operation can suffice and, because the portions of tissue on which the stretching has been performed are moved towards each other as closely as desired and even so as to come edge-to-edge, the scar where said edges are united can be reduced to a minimum so as to leave as little visible trace as possible.

Furthermore, the area of the support used (e.g. a plate) may be greater than the area defined by the edges of the regions of tissue to be stretched, and along which the fastening means are located, which can make it possible to detach the tissue behind the fastening lines of the device, thereby facilitating lengthening of the tissue being stretched. Since the or each support is stationary compared with the tissue and therefore should not move with the tissue, regardless of the area of the support, the supports do not hinder in any way the traction effect of the fastening means and the stretching of said tissue, and indeed, on the contrary, when a plurality of supports are used instead of a common support, the large area of the supports makes them that much easier to keep stationary without any need to fix the supports to one another.

Furthermore, the existence of a support plate that can be deformed into the desired shape, e.g. the shape of the skull of the person whose scalp is to be treated, ensures that the resilient means and the fastening means are very well guided, and makes the system much easier to put into place than previously known systems; Likewise, the resilient means and elements may be fixed on said plate(s) in adjustable manner providing the possibility of adaptation to the morphology and to the desired result, depending on the person concerned.

As already mentioned in the prior application, a plurality of devices and fastening systems that may be installed simultaneously can be used in combination, thus making it possible to pull on certain regions in succession in a well determined order: for example, a first device of the kind described in the preceding application may be used with a common support for the fastening system, but enabling much greater elongation to be performed, thereby enabling regions of tissue that are very far apart to be treated while applying considerable traction force thereto, and a second device, this time in accordance with the present invention, may be interposed between the fastening systems of the preceding device, applying a traction force that is smaller and enabling the edges of the regions concerned finally to be brought together.

It can also be seen that the time required for treatment is reduced to even less than that required when using prior devices. In this way the overall cost of treatment is further reduced, as is the pain to which the person concerned is subjected, which person is encouraged by the area of eliminated bald scalp being greater than when using any previously known devices or methods.

Other advantages of the present invention could also be mentioned, but those mentioned above are already sufficient for demonstrating the novelty and the advantage of the invention.

The following description and figures relate to examples of the invention, but they are not limiting in any way. Other embodiments are possible within the ambit of the scope and of the extent of the present invention, in particular by changing the shape and the type of the resilient means and the shape and the type of the fastening means and of the common support. It may be observed that the following description and figures, and also the explanations above, all relate essentially to the main application of the invention to reducing baldness. However it is clear that all devices of the present invention can be used in other types of application that require or involve the stretching of tissue, in particular making skin firmer or repairing regions that have been destroyed or injured. Naturally, it is possible to use devices of the invention not only beneath the skin as described below, but also on the outside of the tissue concerned, which although less attractive may be entirely satisfactory in certain applications.

BRIEF DESCRIPTION OF THE DRAWINGS

FIG. 1 is a diagrammatic perspective view of the device of the invention implanted on the head.

FIG. 2 is a fragmentary section view showing the fastening of a device beneath the scalp.

FIG. 3 is a perspective view of an embodiment of the device at rest.

FIG. 4 is a perspective view of the device of FIG. 3 in its semi-extended position.

FIG. 5 is a profile view of another embodiment of the device of the invention having a central slot and shown at rest.

FIG. 6 is a perspective view of the FIG. 5 device in a semi- or totally-extended position.

FIG. 7 is a perspective view of the same device as in FIGS. 5 or 6, but with fastening supports in the form of a comb, the device being shown in its position prior to beginning extension, or in the last stage of bringing edges together.

FIG. 8 is a perspective view of another embodiment of the device of the invention shown in its rest position.

FIG. 9 is a perspective view of the FIG. 8 device shown in its position of maximum extension.

FIG. 10 is a perspective view of another embodiment of the device of the invention.

FIG. 11 is a fragmentary section view through the device of FIG. 10.

MORE DETAILED DESCRIPTION

FIG. 1 is a diagrammatic perspective view of the head of a person whose scalp includes a bald region 1, and hair-carrying regions 3 situated at the periphery of the bald region 1.

The extender device 2 of the present invention is then disposed beneath said scalp, by incision of an opening 14 in the middle of said bald region 1. The fastening systems situated at the two ends of the resilient means of the device 2 shown herein as a rectangle, and comprising hooks 7, for example, are anchored in the galea 6 and in the hypoderma, that is to say the rigid fiber layer constituting the deepest portion of the scalp, shown in section in FIG. 2.

Said fastening systems 7 which may be constituted by hooks but which could be any other system for taking hold of tissue, are thus installed along the edges 13 of at least a portion of the area of tissue to be treated, and in this case the example is the scalp where the purpose is to move the hair-carrying regions 2 towards each other. These edges 13 are not necessarily exactly at the boundary 16 between hair-carrying regions 3 and the bald region 1. However, according to the present invention, that boundary position is not only possible but is preferable, as indicated above, such when extension is complete and the extender 2 has returned to its rest position, the fastening systems 7 are situated against each other, and there is therefore no need for margins 17 of hair-carrying scale initially to be situated in between the fastening systems when the device is put into place. It is thus possible for the boundary edges 16 between the hair-carrying regions and the bald region 1 to coincide with the edges 13 of the region to which the fastening systems 7 are secured so as to stretch the entire hair-carrying region 3.

As in the preceding patent application, it is no longer necessarily useful or appropriate to apply continuous and uniform force to the entire length of the edges 13 of the area to be treated. It may be possible to apply traction and fastening only to a fraction thereof in non-adjacent zones, depending on the state of the tissue and on the desired result, and this may be done, for example, by having extender devices of shapes that do not necessarily include fastening systems disposed in continuous straight lines. The fastening systems may be curved, discontinuous, etc. . . . , as known from the document mentioned in the introduction. Adjacent regions lying between two traction points or lines will be pulled indirectly to a greater or lesser extent depending on the disposition of the fastening systems 7, and thus, even if traction is applied only to a fraction of the edges 13 of the region to be treated, the entire region will be subjected to extension, but in a manner that is selective, determined, and defined, thereby making it possible to obtain the best desired result.

In FIG. 1 the extender device or "extender" is made in the manner shown in FIGS. 3 to 11, for example, and it is put under tension on being installed by means of tools such as those shown and described in prior patent application mentioned in the introduction. Resilient means 8 such as those described below will then pull progressively in their direction of active resilience XX' in which they have themselves been stretched, so as to return to their initial length, thereby moving the fastening systems 7 towards each other and thus tending to bring together said edges 13 while compressing the bald region 1 situated between them, and this will continue until the said edges 13 meet if that is so desired or until they reach a predetermined desired separation distance. Naturally, the lengths of the resilient means may be designed so that, at rest, they leave a certain desired distance between the edges 13, depending on the type of application and on the desired result, as indeed is true of the devices in the prior patent. Confidential experiments have shown that this extension/compression can be achieved in a period of time of the order of one month. Such extension/compression can be total when it is desired that the edges 13 should come together completely, as applies particularly when the edges 13 coincide with the edges 16 of the hair-carrying regions.

The scar 14 through which said device was installed, can then be reopened to remove the device and cut off the bald strip 1 which is then naturally in excess, after which the edges 16 are sewn directly together. The desired effect, namely uniform stretching of the hair-carrying regions, has thus been obtained, and no further operation is required.

FIG. 2 is a section through the scalp in which the device of the invention has been anchored by one of its fastening systems $7_1$ engaging in the galea and the hypoderma 6, i.e. the fibrous surface situated beneath the scalp 5 proper, and itself protected by the outer skin 4. In the example of FIG. 2, the device shown is the device of FIGS. 3 and 4, where the fastening systems $7_1$ tend to pull the edges 13 of regions outside the region to be treated 3, thus applying traction force to them by the resilient means $8_1$, while simultaneously the zone situated inside said edges 13 is in compression. The resilient means $8_1$ crosses through the resilient means $8_2$ to which the other fastening system $7_2$ (not shown) is secured, with the set of said resilient means $8_1$ and $8_2$ being fixed at one end each and being guided by the support plate 9 which is situated beneath them and which keeps them against the scalp 6. In FIG. 2, the support plate 9 is shown as being larger in area than the area defined by the edges 13 of the tissue to be treated and along which the fastening means 7 are positioned. It would also be possible to envisage having only half an active extender device with only one resilient means under tension, and with both fastening systems anchored in the tissue to be treated. Under such circumstances, the support plate 9 would be held in place by any suitable means such as merely being sufficient area to be held in place by friction against the surrounding tissue while leaving the tissue that is subjected to traction free to stretch without impediment, and the fastening system (one of whose resilient means is not under tension) could optionally be secured relative to said support plate, and under such circumstances, it is possible to stretch only one side of the tissue, namely the side corresponding to the single edge on which the fastening means is free to move.

In the embodiments shown in FIGS. 3 to 11, the devices 2 for extending living tissue, such as the scalp, mentioned by way of example as the main application in FIGS. 1 and 2, comprise in known manner, at least one resilient means 8 and at least two fastening means 7 enabling the device 2 to be fastened within the tissue along the edges 13 of the area thereof that is to be treated, which edge are opposite to each other in the direction in which they move towards each other under drive from at least one of said resilient means 8.

Furthermore, the extender device 2 of the invention includes at least two independent resilient means 8, each fixed at at least one end to at least one of said fastening means 7, and at least one support 9 that may be common, quasi-rigid, and stationary compared with said tissue, e.g. by the frictional resistance between its area and the surrounding tissue. The support 9 is connected to at least one of said resilient means 8, which means deform by moving relative to said support against which they drive said fastening means 7 towards each other.

Said support 9 is made of a biocompatible material, e.g. titanium, and it is preferably common to the resilient means and it is additionally kept stationary by the effect of the mutual reaction of the resilient means on opposite ends thereof such that the forces act against each other; said support(s) may be deformable thin plates suitable for being deformed so as to take up a rounded shape as shown in FIGS. 3 to 9 that matches the shape of said tissue 5 to be treated, e.g. the scalp, in which case it takes up the shape of a skull. When the support is a single, common plate, which may be solid or which may have openings, the other ends of said resilient means 8 that are not secured to the fastening means 7 are fixed to the plate.

The support plate 9 may also be constituted by at least two superposable supports or plates each associated with a respective resilient means 8 and fastening means 7, which plates or supports are placed adjacent to each other in order to obtain a given length that is thus adjustable. There is no need to fasten them together if they are of sufficient area to ensure that each of them is kept stationary compared with the tissue by friction, as mentioned above.

In FIGS. 3 and 4, said resilient means 8 are constituted by parallel elastic strips that are spaced apart from each other such that one of said resilient means $8_2$ is constituted by a single strip passing freely between two outer strips constituting the other resilient means $8_1$ and corresponding in width to the fastening system $7_1$. However, it would also be possible or the resilient means $8_1$ to be made up of three or four or even more strips and for the resilient means $8_2$ then to be in the form of two or three or more corresponding strips, or vice versa. The ends of the strips $8_2$ are fixed firstly towards a first end edge $20_2$ of the support plate 9 and secondly to one of the fastening means $7_2$ such that extension of said resilient means $8_2$ makes it possible to displace said fastening means $7_2$ towards the opposite other strips $8_1$ are fixed in similar manner firstly to said second end edge $20_1$ and secondly to the other fastening means $7_1$ such that the resilient means $8_1$ associated therewith makes it possible for the other fastening means $7_1$ to be displaced towards the first edge $20_2$ of the support 9.

In FIG. 3, the device as described above is shown in its rest position, as is the device in FIG. 5, with the length of the elastic strips $8_1$ and $8_2$, making it possible for example, to bring the fastening systems 7 into edge-to-edge contact.

In FIG. 4, the device is shown in its semi-extended position on being installed, with the fastening system $7_2$ having been passed between the strips $8_1$ of the resilient means carrying the fastening system $7_1$ so as to enable said fastening means to be pulled to a maximum extent towards the edges $20_1$ and $20_2$ of the support plate 9, or even beyond them, or possibly not quite so far as the said edges, depending on the desired distance. Once the fastening means have been hooked into the tissue to be treated, the resilient means tend to urge the fastening means 7 towards each other, as described above.

Clearly, when a plurality of strips are used in each of the resilient means $8_1$ and $8_2$, then they must remain in mutual engagement even in the rest position and they are incapable of being disengaged (as shown in FIG. 3) since that is possible only when one of the means has one strip and the other has two.

In FIGS. 5 to 7, said support plate 9 includes at least one transverse slot 11 extending parallel to the directions of the fastening means 7 along the edges 13 of the tissue to be treated. Each of the resilient means 8 extends from the same edge 20 of the support 9 as the associated fastening means, but over the opposite face of the support, passing through the slot and back over the same face of the support 9 as the associated fastening means, where they are fixed to the fastening means 7. In this embodiment, each of the resilient means $8_1$ and $8_2$ can be constituted by two strips, like the means $8_1$ in FIGS. 3 and 4, the ends of both strips being fixed to the corresponding fastening systems 7. However they could alternatively be multistrip means or they could even be constituted by a single sheet of resilient material covering the entire width of the fastening system 7. The area and the quantity of the strips depends on the desired lengthening length and on the desired resilient stiffness, it being desirable for the resilient means to be as thin as possible but not so thin as to become fragile since they could then tear. In addition, the said support plate 9 could include rounded thrust surfaces 12 on either side of said slot 11, e.g. in the form of mini-rollers, against which said resilient means 8 can slide going over the corresponding rounded portion without any risk of tearing.

In FIG. 7, the supports 15 of the fastening means 7 are shown as being in the form of combs with said hooks being disposed at the each comb being fixed to the end of one of the resilient means 8. The comb teeth of the support 15 for the fastening means 7 may be designed to interdigitate when the fastening means are brought close together by said resilient means 8. Naturally, such comb systems could be adapted to any device of the invention as shown herein, whenever it is desired to bring the edges of the tissue to be treated directly into contact. For example, in the embodiment shown in FIGS. 3 or 4, the outer edges on which the hooks 7 are located cannot be brought closer together than the width of the supports 15 when the supports come into contact with each other.

In FIGS. 8 and 9, said resilient means 8 are constituted by systems of springs 10 co-operating with guides 18 secured to the support plate 9 and along which said springs are compressed and then allowed to relax when the fastening means 7 are moved apart and then allowed to move towards each other by the action of said springs 10.

In FIG. 8, said springs 10 are shown in their relaxed position, in which case the hooks 7 may be disposed along the edges of their touching supports 15, pointing away from the corresponding springs 10, thus enabling the hooks to be very close together, and much closer together than is possible using resilient means that work in traction. The supports 15 associated with the springs of FIG. 8 are situated behind the hooks so as to bear against said springs 10 which are then situated on the same side as the corresponding fastening systems that can then be displaced relative to the central portion where the connection line of the tissue to be treated must be located relative to the support plate 9, whereas when using flexible resilient means that work in traction, the positions of the supports 15 are the other way round relative to said line.

In FIG. 9, said springs 10 are shown fully compressed and the fastening systems 7 together with their supports 15 are then in their furthest-apart position, in which position they also receive maximum thrust force from the springs 10 urging them towards the central portion of the plate 9.

FIG. 10 shows another embodiment of an extender device of the present invention comprising at least four supporting and guiding wheels 19 for resilient means 8 that may be of rounded section and that pass in grooves of said pulleys 19, as shown in FIG. 11. These resilient means 8 are fixed at opposite ends to the ends of the supports 15 of the fastening systems 7. Thus, by pulling on said supports 15, the resilient means 8 are stretched, and lengthening thereof makes it possible for them to run around the supporting wheels 19 until the desired distance is achieved. Each resilient means 8 associated with said fastening system 7 is associated with two wheels situated at the two ends of said fastening system 7, and since the axes YY' of the set of wheels are parallel in pairs and secured by any appropriate means to one another in fixed manner. In this case, there is no genuine guiding support for said fastening means 7, but only the resilient means 8. Such an embodiment is therefore not the best for achieving the aim of the problem posed, but it satisfies the characteristics of the present invention as defined above.

The set of pulleys 19, supporting pulley axes, and fixing means therefor thus constitutes the common support 9 of the invention, and it can be relatively thin if said pulleys are situated in the same plane. However it could be made thicker by stacking the pulleys of the two fastening systems 7 in pairs one above the other at each end of said fastening systems 7, thereby enabling them to be brought closer together, even though that is to the detriment of the thickness of said support 9.

FIG. 11 is a section view AA' through one of the pulleys 19 of FIG. 10.

The resilient means shown in FIGS. 3, 4, 5, 6, 7, 10, and 11 are flexible parts made of biocompatible material, and preferably of a silicone type elastomer. They may be capable of lengthening by more than 100% of their length at rest, which, when using a plate type support as shown in FIGS. 3 to 7, makes it possible to fasten the fastening systems 7 beyond the ends of the support 9. In such embodiments, it is also possible to provide for the resilient means 8 to be capable of being fixed to the support plate(s) 9 in a plurality of different positions, e.g. by engaging studs secured to a plate in holes occupying a plurality of rows in the resilient means. It is thus possible to displace the fixing of such resilient means relative to the support plate(s) thereby adapting their lengths and rest positions at the end of stretching to the morphology of the patient and to the desired outcome.

We claim:

1. A device for permanently stretching a selected area of skin tissue, said skin tissue having an underneath side formed of one of a galea and hypoderma region and an outer surface comprising:

an integrally formed support plate having first and second ends and a mid-section therebetween and made from a semi-rigid biocompatible material;

at least two resilient means for placing skin tissue under a continuous tensile stretching force, each of the resilient means having a fixed end and a free end, each of the fixed ends of the resilient means respectively fixed to one of the ends of the support plate, each of the resilient means having a pre-biased resting length and a biased extended length, each of the resilient means being biased by displacement of the free end toward the end of the support plate opposite that resilient means fixed end;

at least two fastening means for securing skin tissue to the resilient means without sutures, each of the respective fastening means being attached to a respective free end of the resilient means and each of the fastening means adapted to be fixedly located along a respective region of skin tissue thereby defining respective lines of traction, wherein skin tissue to be stretched within each region is laterally outward of each of said lines of traction, said skin tissue regions opposed to each other and separated by an extent of skin tissue that is not to be stretched;

the mid-section of said support plate corresponding to the pre-biased resting length for each of the free ends of the resilient means when each of the resilient means are respectively at a pre-biased resting position, each of the resilient means disposed closely along a surface of the plate;

the plate adapted to be deformed into a contour matching underlying coextensive tissue underneath the skin tissue and being stationary relative to the underlying tissue when the device is implanted and operable under the skin tissue, the resilient means guides along the contour of the plate to closely follow the shape of the underlying coextensive tissue, wherein each of the fastening means grip the skin tissue from said underneath side thereof and along a respective line of traction without extending through said outer surface of the skin tissue, each of the resilient means being at a biased extended position when initially fastened to said skin tissue and continuously exerting a force on the fastening means thereafter, thereby urging the lines of traction toward each other while stretching the skin tissue which lies outward of said lines of traction, until each of the resilient means returns to its respective pre-biased resting position, said skin tissue between the lines of traction being left unstretched.

2. The device according to claim 1, in which said resilient means is comprised of first and second strip parallel resilient strips, each of said strips having a respective first and a second end, said first strip being U-shaped and having a pair of legs corresponding to said first end, said second strip freely passing between the legs of said U-shaped first strip, the second ends of each of said strips being fixed on opposite ends of the plate and said first ends of each of said strips fixed to a respective said fastening means such that extension of the resilient means enables each of said fastening means to be respectively displaced towards the opposite plate end from its respective fixed end.

3. The device according to claim 1, in which said resilient means are flexible pieces of silicone elastomer material.

4. The device according to claim 1, wherein the resilient means are a plurality of springs, each of the springs cooperating with a respective guide formed in said plate and along which said springs are initially compressed and then allowed to expand, thereby stretching said skin tissue.

5. The device according to claim 1, in which the plate laterally extends beyond said opposed skin tissue regions and said lines of traction.

6. The device according to claim 1, in which each of the fastening means is comprised of hooks, said hooks being fixed to corresponding ends of the resilient means, which fastening means are suitable for an interdigitated relationship when said fastening means are moved together by said resilient means.

7. The device of claim 1, wherein the resilient means is comprised of a pair of resilient means each having a respective first and second end, each first end of the resilient means respectively fixed to opposite ends of the support plate and wherein a respective fastening means is coupled to a respective said second end on each of said resilient means, each of said resilient means interdigitated so as to be movable toward each other by the resilient means.

8. The device of claim 1, wherein one of said resilient means has a first end fixed to one of said ends of the support plate, and the other of said resilient means has a first end fixed to the other end of said support plate, each of said resilient means having a respective second and free end coupled to a respective said fastening means, each of said fastening means having hooks extending away from its respective first and fixed end, where each resilient means pushes its fastening means away from its respective first and fixed end, thereby stretching said tissue relative to the support plate.

9. The device according to claim 1, wherein said skin tissue can be stretched a distance which can vary, said distance at most extending from said line of traction to said resting position.

10. The device for stretching skin tissue as claimed in claim 1, said plate extending laterally beyond said opposed skin regions and said lines of traction.

* * * * *